(12) United States Patent
Minami

(10) Patent No.: US 8,071,177 B2
(45) Date of Patent: Dec. 6, 2011

(54) SUBSTRATE AND METHOD FOR PRODUCING THE SUBSTRATE

(75) Inventor: Koichi Minami, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/651,689

(22) Filed: Jan. 4, 2010

(65) Prior Publication Data

US 2010/0173326 A1 Jul. 8, 2010

(30) Foreign Application Priority Data

Jan. 5, 2009 (JP) ................................. 2009-000114

(51) Int. Cl.
*B05D 1/36* (2006.01)
*G01N 33/53* (2006.01)
(52) U.S. Cl. ...................... 427/419.1; 435/7.1
(58) Field of Classification Search .................. None
See application file for complete search history.

(56) References Cited

U.S. PATENT DOCUMENTS 6,197,515 B1 * 3/2001 Bamdad et al. .................. 435/6

OTHER PUBLICATIONS

Valiokas et al., "Differential Protein Assembly on Micropatterned Surfaces with Tailored Molecular and Surface Multivalency," ChemBioChem, 2006, vol. 7, Issue 9, pp. 1325-1329.*
Löfås et al., "The art of Immobilization for SPR Sensors," Springer Ser Chem Sens Biosens 2006, vol. 4, pp. 117-151.*
Sigel et al., "A Self-Assembled Monolayer for the Binding and Study of Histidine-Tagged Proteins by Surface Plasmon Resonance," Anal. Chem., 1996, vol. 68, No. 3, pp. 490-497.*
"High Affinity Chelator Thiols for Switchable and Oriented Immobilization of Histidine-Tagged Proteins: A Generic Platform for Protein Chips Technologies", A. Tinazli et al., Chem. Eur. J., vol. 11, pp. 5249-5259, 2005.
"Production of Histidine Tagged Protein Arrays and Label Free Interaction Observations", M. Kyo and T. Natsume, Toyobo Life Science Magazine, vol. 77, pp. 15-16, 2004.
Applications, Properties and Synthesis of ω-Functionalized n-Alkanethiols and Disulfides—the Building Blocks of Self-Assembled Monolayers, D. Witt et al., Curr. Org. Chem. vol. 8, pp. 1763-1797, 2004.
"Zwitterionic SAMs that Resist Nonspecific Adsorption of Protein from Aqueous Buffer", R.E. Hollin et al., Langmuir, vol. 17, pp. 2841-2850, 2001.
"A Survey of Structure-Property Relationships of Surfaces that Resist the Adsorption of Protein", E. Ostuni et al., Langmuir, vol. 17, pp. 5605-5620, 2001.
"Self-Assembled Monolayers That Resist the Adsorption of Proteins and the Adhesion of Bacterial and Mammalian Cells", E Ostuni et al., Langmuir, vol. 17, pp. 6336-6343, 2001.
"Self-Assembled monolayers of Thiolates on Metals as a Form of Nanotechnology", J.C. Love et al., Chemical Review, vol. 105, pp. 1103-1169.

* cited by examiner

*Primary Examiner* — Shafiqul Haq
*Assistant Examiner* — Galina Yakovleva
(74) *Attorney, Agent, or Firm* — Young & Thompson

(57) ABSTRACT

A self assembling monolayer formed by the self assembling molecules is caused to bond onto the surface of a base material, and chelators are caused to bond onto the self assembling monolayer, to produce a substrate, in which the chelators are bound to the self assembling monolayer at a density within a range from 0.4/nm$^2$ to 4/nm$^2$. The bonding of the chelators onto the self assembling monolayer being performed within an organic solvent.

13 Claims, 3 Drawing Sheets

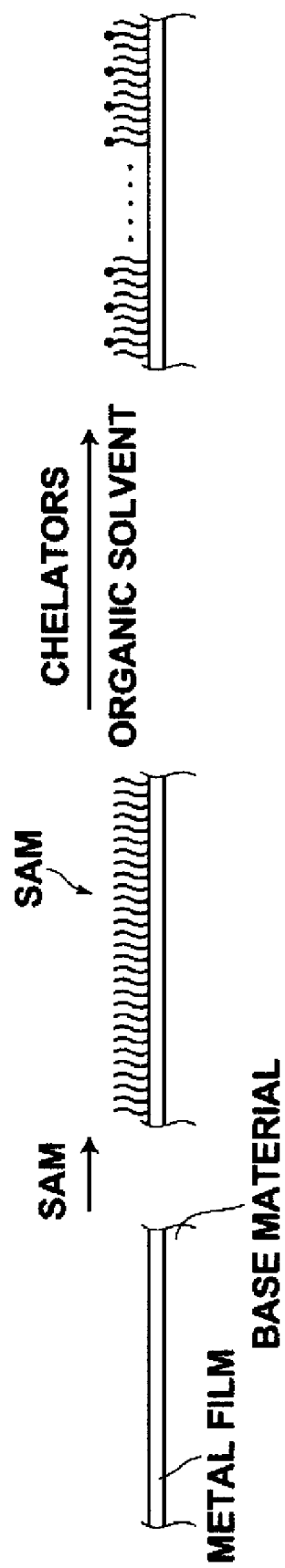

SUBSTRATE AND METHOD FOR PRODUCING THE SUBSTRATE

BACKGROUND OF THE INVENTION

1. Field of the Invention

The present invention is related to a substrate onto which bioactive substances can be favorably immobilized. The present invention is also related to a method for producing the substrate. Further, the present invention is related to a biosensor chip and a bioreactor chip equipped with the substrate.

2. Description of the Related Art

Presently, measurements that utilize intermolecular interactions, such as immune reactions in clinical tests, are being performed. Several techniques that do not require complex operations or labeling substances, and are capable of detecting variations in the bonding amounts of measurement target substances at high sensitivity, are being utilized. Examples of these techniques include: the Surface Plasmon Resonance (SPR) measurement technique, the quartz crystal microbalance (QCM) measurement technique, and a technique that utilizes the functional surfaces of gold colloid particles to superfine particles. In all of these techniques, surfaces on which bioactive substances are immobilized are necessary. This will be explained, using Surface Plasmon Resonance (SPR) as an example.

Commonly, measurement chips which are utilized to measure bioactive substances comprise: a transparent substrate (a glass plate, for example); a metal film formed by vapor deposition on the transparent substrate; and a thin film having functional groups onto which bioactive substances such as proteins can be immobilized; stacked in this order. Bioactive substances are immobilized onto the surface of the metal film via the functional groups. Specific bonding reactions between the bioactive substances and targets of measurement are measured, to analyze the interaction among biomolecules. Accordingly, improvements in bonding between the bioactive substances and the target measurement substances are desired in measurement chips.

SAM's (Self Assembling Monolayers), which have a constant regularity formed by mechanisms of the film material itself, without detailed control being exerted from the exterior, are examples of a thin film of a measurement chip that has functional groups capable of immobilizing bioactive substances. For example, "High-Affinity Chelator Thiols for Switchable and Oriented Immobilization of Histidine-Tagged Proteins: A Generic Platform for Protein Chip Technologies", A. Tinazli et al., Chem. Eur. J., Vol. 11, pp. 5249-5259, 2005 discloses a technique by which SAM's are formed by a reagent having multivalent chelate thiol residues. In addition, "Production of Histidine Tagged Protein Arrays and Label Free Interaction Observations", M. Kyo and T. Natsume, Toyobo Life Science Magazine, Vol. 77, pp. 15-16, 2004, discloses a technique for producing a two dimensional NTA film, by producing a SAM having carbonic acid at the ends thereof, then modifying the SAM with NTA in water.

However, the SAM disclosed in Chem. Eur. J. is a single component SAM formed by bis-NTA (bis-Nitrilotriacetic acid) or a mixed SAM formed by bis-NTA and a reagent having an OH group at the ends thereof. Therefore, the ends of the SAM become bulky, the SAM cannot be packed onto a metal film in an organized state, and gaps and defects in the SAM are likely to occur on the metal film. Therefore, there is a problem that non specific adsorption onto the metal film cannot be suppressed. In order to improve specific bonding between bioactive substances and detection target substances, it is effective to hold the bioactive substances at many points. However, because the NTA disclosed in Chem. Eur. J. is a bulky functional group, the SAM becomes rigid and not capable of moving flexibly. Accordingly, it is difficult for metal to coordinately bond with the bioactive substances at many points, and there is a problem that the bioactive substances cannot be stably immobilized at many points. Meanwhile, the modification method disclosed by M. Kyo and T. Natsume is not capable of binding NTA at a density sufficient to induce bonding at multiple points.

SUMMARY OF THE INVENTION

The present invention has been developed in view of the foregoing circumstances. It is an object of the present invention to provide a substrate which is capable of stably immobilizing bioactive substances thereto, while suppressing non specific adsorption. It is another object of the present invention to provide a method for producing the substrate. It is another object of the present invention to provide a biosensor chip and a bioreactor chip equipped with the substrate.

The substrate of the present invention comprises:

a base material;

a self assembling monolayer formed by self assembling molecules which are bound onto the surface of the base material; and chelators which are bound onto the self assembling monolayer; and is characterized by:

the chelators being bound to the self assembling monolayer at a density within a range from $0.4/nm^2$ to $4/nm^2$.

It is preferable for the chelators to be nitrilotric acetic acid derivatives.

It is preferable for metal ions to be immobilized onto the chelators.

It is preferable for bioactive substances to be immobilized onto the metal ions.

It is preferable for the metal ions to be transition metal ions, and more preferable for the metal ions to be Cu(II) ions.

It is preferable for the bioactive substances to have functional groups that coordinately bond with the transition metal ions, and are immobilized onto the transition metal ions by the functional groups.

It is preferable for the functional groups to be imidazole groups.

A method for producing the substrate of the present invention comprises the steps of:

bonding the self assembling monolayer formed by the self assembling molecules onto the surface of the base material; and bonding the chelators onto the self assembling monolayer; and is characterized by:

the bonding of the chelators onto the self assembling monolayer being performed within an organic solvent.

It is preferable for the organic solvent to be an aprotic polar solvent. It is more preferable for the organic solvent to be selected from a group consisting of: dimethyl sulfoxide and N,N-dimethyl formamide.

The substrate of the present invention may be favorably applied to a biosensor chip or a bioreactor chip.

The substrate of the present invention is equipped with the base material and the self assembling monolayer formed by the self assembling molecules which are bound onto the surface of the base material; and the chelators which are bound onto the self assembling monolayer. The chelators are bound to the self assembling monolayer at a density within a range from $0.4/nm^2$ to $4/nm^2$. Therefore, it is possible for the chelators to hold bioactive substances at multiple points, and the bioactive substances can be stably immobilized. In addition, the substrate of the present invention has the self assembling monolayer formed by the self assembling molecules. Therefore, the self assembling monolayer is packed onto a metal film in an organized state, without any gaps or defects in the SAM on the surface of the metal film, and it is possible to suppress non specific adsorption.

The method for producing the substrate of the present invention comprises the steps of: bonding the self assembling monolayer formed by the self assembling molecules onto the surface of the base material; and bonding the chelators onto the self assembling monolayer. The bonding of the chelators onto the self assembling monolayer is performed within an organic solvent. Therefore, it is possible to bind the chelators onto the self assembling monolayer at a density within a range from $0.4/nm^2$ to $4/nm^2$. Accordingly, a substrate that can hold bioactive substances by chelators at multiple points and stably immobilize the bioactive substances thereon can be produced.

BRIEF DESCRIPTION OF THE DRAWINGS

FIG. 2 is a schematic diagram that illustrates the steps for producing the substrate according to an embodiment of the present invention.

DESCRIPTION OF THE PREFERRED EMBODIMENTS

Figure 1:
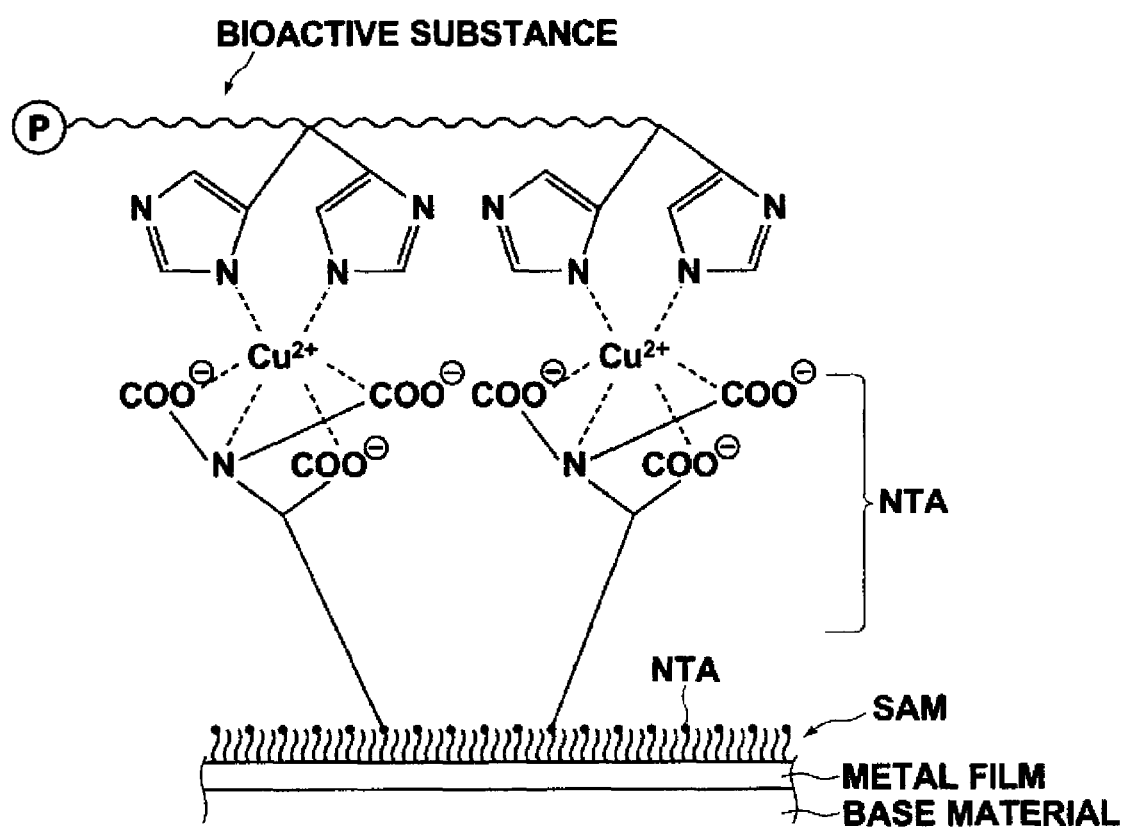
FIG. 1 is a schematic diagram that illustrates the structure of a substrate according to an embodiment of the present invention.

Hereinafter, the substrate of the present invention will be described with reference to the attached drawings. FIG. 1 is a schematic diagram that illustrates the structure of a substrate according to a first embodiment of the present invention. Note that FIG. 1 is magnified to clearly illustrate bonding states. NTA is employed as the ligands, Cu(II) is employed as the metal ions, and proteins having imidazole groups as function groups are employed as the bioactive substance (denoted by P in FIG. 1). A state in which pairs of NTA's are bound to the proteins via the imidazole groups is illustrated in FIG. 1.

The substrate illustrated in FIG. 1 is equipped with a base material, on the surface of which a metal film is provided. A self assembling monolayer (SAM) formed by self assembling molecules is formed on the metal film. Chelators are bound to the self assembling monolayer at a density within a range from $0.4 \ nm^2$ to $4/nm^2$. The chelators and the proteins P having the imidazole groups are capable of bonding with a plurality of Cu(II) ions. Therefore, the proteins P can be stably immobilized.

The SAM (Self Assembling Monolayer) provided on the surface of the base material is formed by self assembling molecules having a constant regularity formed by mechanisms of the film material itself. The self assembling molecules do not have groups having large thicknesses at the ends thereof. Therefore, the self assembling monolayer is packed onto the metal film in an organized state, without any gaps or defects in the SAM on the surface of the metal film, and it is possible to suppress non specific adsorption.

Hereinafter, each of the structures of the biosensor chip of the present invention and the methods for forming (activating) the structures will be described.

(1) Base Material

In the case that use in a surface plasmon resonance biosensor is considered, materials which are transparent with respect to laser beams may be utilized as the material for the substrate of the biosensor chip. Examples of such materials include: optical glass, such as BK7; and synthetic resin, such as polymethyl methacrylate, polyethylene terephthalate, polycarbonate, and cycloolefin polymer. It is desirable for the base material to be formed by a material that does not exhibit anisotropy with respect to polarization, and is superior in workability.

The metal film is provided on the base material. Here, "provided on the base material" includes cases in which the metal film is in indirect contact with the base material via another layer, that is, without directly contacting the base material, in addition to cases in which the metal film is in direct contact with the base material. The metal to be utilized as the material of the metal film is not particularly limited, as long as it is capable of generating surface plasmon resonance. However, it is preferable for the material to be at least one metal, selected from a group consisting of: gold, silver, copper, platinum, palladium, and aluminum. Gold is particularly preferred. These metals may be used singly or in combination. In addition, an intermediate layer of chrome, for example, may be interposed between the substrate and the metal film.

The thickness of the metal film may be set as desired. However, it is preferable for the thickness of the metal film to be within a range from 0.1 nm to 500 nm, and more preferably within a range from 1 nm to 200 nm. This is because surface plasmon phenomena of media cannot be sufficiently detected if the thickness of the metal film exceeds 500 nm. In the case that the intermediate layer of chrome or the like is interposed between the substrate and the metal film, the thickness of the interposed layer is preferably within a range from 0.1 nm to 10 nm.

In the case that the substrate is to be employed in a bioreactor, the base material may be formed by glass, metal oxides, or synthetic resins. Specific examples of the material for the base material include: sepharose; polyethylene; polystyrene; poly (meth) acrylic acid; poly (meth) acryl amide; polymethyl (meth)acrylate; polyethylene terephthalate; polycarbonate; and cycloolefin polymers. It is preferable for a material which is stable under conditions in which bioreactors are utilized to be employed as the material of the base material.

In the case that the substrate is to be employed in a bioreactor, the metal film is not necessary. However, in the case that the metal film is to be provided, metals similar to those employed by the substrate for the aforementioned biosensor may be employed. It is preferable for the thickness of the metal film to be within a range from 0.1 nm to 1 μm, and particularly to be within a range from 1 nm to 100 nm. An intermediate layer formed by chrome or the like may be provided in a manner similar to that of the aforementioned biosensor. It is preferable for the thickness of the intermediate layer to be within a range from 0.1 nm to 10 nm.

(2) Self Assembling Monolayer

SAM's (Self Assembling Monolayers) refer to ultrathin films, Such as monomolecular films and LB films, which have uniform regularity imparted by the mechanism of the film material without detailed external control being exerted, and are formed by self assembling molecules. The self assembling molecules are do not have bulky groups at the ends thereof, and therefore, gaps and defects in the SAM are not likely to occur on the metal film when the self assembling monolayer is formed. That is, the self assembling molecules are packed in an organized manner. More specifically, the self assembling molecules have a functional group, selected from a group consisting of a hydroxyl group, a carboxyl group, an alkoxy group, a methyl group, and an amino group at first ends thereof, and a compound having a functional group, selected from a group consisting of: —SH (thiol), —SS (sulfide), —SeH (selenol), —SeSe (diselenide), and —COSH (thioic acid) at the second ends thereof. The self assembling properties of the self assembling molecules form regular structures and patterns over a great distance under nonequilibrium conditions.

Coating methods for metal films using self assembling monolayers have been developed by Professor Whitesides et al. of Harvard University. The details thereof are reported in "Self-Assembled monolayers of Thiolates on Metals as a Form of Nanotechnology", J. C. Love et al., Chemical Review, Vol. 105, pp. 1103-1169, 2005, for example. In the case that gold is used as the metal, an alkanethiole derivative represented by General Formula A-1 (n represents an integer from 3 to 20, and X represents a functional group in General Formula A-1) may be employed as an organic layer forming compound. In this case, a monomolecular film having uniform orientation is formed in a self assembling manner, based on As—S bonds and van der Waal forces among alkyl chains. The self assembling monolayer can be produced by a simple technique of immersing a gold substrate within a solution containing the alkanethiol derivative. By forming the self assembling monolayer employing a compound represented by General Formula A-1, in which X represents $NH_2$, it becomes possible to coat the surface of the gold film with an organic layer having amino groups.

$HS(CH_2)_nX$          General Formula A-1

The alkanethiol having amino groups at the ends thereof may be a compound represented by General Formula A-2 (n represents an integer from 3 to 20 in General Formula A-2), in which thiol groups and the amino groups are linked via the alkyl chains. Alternatively, a compound in which alkanethiol having carboxyl groups at the ends thereof represented by General Formula A-3 or A-4 (n represents an integer from 3 to 20 in General Formula A-3, and each occurrence of n respectively represents n integer from 1 to 20 in General Formula A-4), which is reacted with a large excess of hydrazide or diamine. The reaction between the alkanethiol having the carboxyl groups at the ends thereof and the large excess of hydrazide or diamine may be performed in a solution state. Alternatively, the alkanethiol having the carboxyl groups at the ends thereof may be bound to the surface of the base material, and then the large excess of hydrazide or diamine may be caused to react therewith.

$HS(CH_2)_nNH_2$          General Formula A-2

$HS(CH_2)_nCOOH$          General Formula A-3

$HS(CH_2)_n(OCH_2CH_2)_nOCH_2COOH$     General Formula A-4

It is preferable for the repetition number of the alkyl groups of the compounds represented by General Formulae A-2 through A-4 to be within a range from 3 to 20, more preferably within a range from 3 to 16, and most preferably within a range from 11 to 16. If the alkyl chains are short, it becomes difficult to form the self assembling monolayer, and if the alkyl chains are long, manufacturing costs increase.

Any desired compound may be employed as the polyamine in the present invention. It is preferable for a water soluble polyamine to be employed in the case that the polyamine is employed on the surface of a biosensor or a bioreactor. Specific examples of water soluble polyamines include: aliphatic diamines, such as ethylene diamine, tetraethylene diamine, octamethylene diamine, decamethylene diamine, piperazine, triethylene diamine, diethylene triamine, triethylene tetraamine, dihexamethylene triamine, and 1,4-diamino cyclohexane; and aromatic diamines, such as paraphenylene diamine, meta phenylene diamine, 4,4'-diamino biphenyl, 4,4'-diamino diphenyl methane, 4,4'-diamino diphenyl ketone, and 4,4'-diamino diphenyl sulfonic acid. It is also possible to employ a compound having pairs of amino groups which are linked by ethylene glycol units, from the viewpoint of improving the hydrophilic properties of the surface of the biosensor or the bioreactor. The diamine to be employed in the present invention is preferably ethylene diamine or a compound represented by General Formula A-5 (n and m respectively represent an integer from 1 to 20 in General Formula A-5), and more preferably ethylene diamine or 1,2-bis(amino ethoxy) ethane (n=2 and m=1 in General Formula A-5).

$H_2N(CH_2)_n(OCH_2CH_2)_mO(CH_2)_nNH_2$    General Formula A-5

The self assembling monolayer may be formed only by the alkanethiol having amino groups. Alternatively, the self assembling monolayer may be formed a mixture of the alkanethiol having amino groups and other alkanethiols. In the case that the self assembling monolayer is formed on the surface of a biosensor, it is preferable for the other alkanethiols to be those that can suppress non specific adsorption of bioactive substances. Professor Whitesides et al. have investigated self assembling monolayers that can suppress non specific adsorption of bioactive substances in detail, and it is reported that self assembling monolayers formed by alkanethiols having hydrophilic groups are effective in suppressing non specific adsorption ("Zwitterionic SAMs that Resist Nonspecific Adsorption of Protein from Aqueous Buffer", R. E. Holmlin et al., Langmuir, Vol. 17, pp. 2841-2850, 2001, "A Survey of Structure-Property Relationships of Surfaces that Resist the Adsorption of Protein", E. Ostuni et al., Langmuir, Vol. 17, pp. 5605-5620, 2001, and "Self-Assembled Monolayers That Resist the Adsorption of Proteins and the Adhesion of Bacterial and Mammalian Cells", E. Ostuni et al., Langmuir, Vol. 17, pp. 6336-6343, 2001).

In the present invention, the compounds described in the research paper above may be employed as the alkanethiol to be mixed with the alkanethiol having amino groups to form the mixed monolayer. It is preferable for alkanethiols having hydroxyl groups represented by General Formula A-6 (n represents an integer from 3 to 20 in General Formula A-6) or alkanethiols having ethylene glycol units represented by General Formula A-7 (n and m respectively represent an integer from 1 to 20 in General Formula A-7) as the alkanethiol to be mixed with the alkanethiol having amino groups to form the mixed monolayer. These compounds are preferred because they are superior in non specific adsorption suppressing functions and because they are readily available. It is preferable for n to be 5 or greater in General Formula A-6, more preferably 10 or greater, and most preferably within a range from 10 to 16.

$HS(CH_2)_nOH$          General Formula A-6

$HS(CH_2)_n(OCH_2CH_2)_mOH$      General Formula A-7

In the case that an alkanethiol having carboxyl groups is mixed with a different alkanethiol to form the self assembling monolayer, it is preferable for the repetition number of the alkyl groups of the compounds represented by General Formulae A-2 through A-4 to be within a range from 4 to 20, more preferably within a range from 4 to 16, and most preferably within a range from 11 to 16.

In the present invention, the alkanethiol having carboxyl groups and the alkanethiol having hydroxyl groups may be mixed at a desired ratio. However, in the case that the ratio of the alkanethiol having carboxyl groups within the mixture is low, the bonding amount of a hydrophilic polymer to be described later will decrease. In addition, in the case that the ratio of the alkanethiol having hydroxyl groups within the mixture is low, the non specific adsorption suppressing function will decrease. For this reason, it is preferable for the ratio of the alkanethiol having the carboxyl groups and the alkanethiol having the hydroxyl groups to be within a range from 1:1 to 1:1,000,000, more preferably within a range from 1:1 to 1:1,000, and most preferably within a range from 1:1 to 1/10. From the viewpoint of the non specific adsorption suppressing function, it is preferable for the molecular length of the alkanethiol having the carboxyl groups to be longer than the molecular length of the alkanethiol having the hydroxyl groups. In addition, alkanethiol having amino groups at the ends thereof may be bound onto the surface of the base material, and then caused to react with a large excess of maleic acid or fumaric acid.

Compounds synthesized based on the teaching of the review paper by Professor Grzybowski of Northwestern University ("Applications, Properties and Synthesis of ω-Functionalized n-Alkanethiols and Disulfides—the Building Blocks of Self-Assembled Monolayers", D. Witt et al., Curr. Org. Chem., Vol. 8, pp. 1763-1797, 2004) and the documents cited therein may be employed as the alkanethiols of the present invention. Alternatively, commercially available compounds may be employed. These compounds are available from Dojin Chemical K.K., Aldrich, SensoPath Technologies, Frontier Scientific Inc., and the like. Disulfide compounds, which are oxidation products of alkanethiol, may be employed in a similar manner to alkanethiol in the present invention.

(3) Chelators

Various chelate solutions may be used as compounds to become the chelators. Preferred examples include polydentate chelators, such as: nitrilotriacetic acid (NTA); iminodiacetic acid; phenanthroline; terpyridine; bipyridine; triethylene tetraamine; bi (ethylene triamine); tris (carboxy methyl) ethylene diamine; diethylene triamine pentaacetic acid; polypyrazolyl boric acid; 1,4,7-triazacyclononane; dimethyl glyoxime; diphenyl glyoxime; and derivatives thereof. Among these, nitrilotriacetic acid and derivatives thereof are preferred. Nitrilotriacetic acid is a quadradentate ligand. Therefore, the chelators are converted to three neighboring carboxyl groups, by the chelators bonding with the functional groups at the end of the self assembling molecules of the self assembling monolayer.

In the case that the functional groups at the ends of the self assembling molecules of the self assembling monolayer are carboxyl groups, the chelators can be caused to bond with the carboxyl groups, by: activating the carboxyl groups; then causing the chelators to react therewith, for example. The carboxyl groups may be activated by a method that employs 1-(3-dimethyl aminopropyl)-3 ethyl carbodiimide (EDC), which is a water soluble carbodiimide, and N-hydroxysuccinimide (NHS), or by a method that employs EDC alone.

It is preferable for an organic solvent to be employed while binding the chelators. The use of the organic solvent enables the chelators to be bound to the self assembling monolayer at a density within a range from $0.4/nm^2$ to $4/nm^2$. In the case that the chelator density is less than $0.4/nm^2$, it is not possible to hold imidazole groups in the vicinity at multiple points. Meanwhile, it is theoretically difficult to bind chelators at a density greater than $4/nm^2$. The chelator density is preferably within a range from $0.4/nm^2$ to $4/nm^2$, more preferably within a range from $1/nm^2$ to $4/nm^2$, and most preferably within a range from $1.2/nm^2$ to $2/nm^2$.

It is preferable for the organic solvent to be an aprotic polar solvent. Examples of such organic solvents include: dimethyl sulfoxide; N,N-dimethyl formamide; N,N-dimethyl acetamide; acetonitrile; N-methylpyrrolidone; acetone; methyl ethyl ketone; methanol; ethanol; isopropyl alcohol; sec-butyl alcohol; tert-butyl alcohol; butyl cellosolve; tetrahydro furane; and diglyme. It is preferable for dimethyl sulfoxide or N,N-dimethyl formamide to be employed, from the viewpoints of the solubility of the chelators and suppression of side reactions.

The chelator density can be determined by the following methods. In the case that actual measurement is performed, the chelators are caused to bind with the base material. Thereafter, metal ions are added, and the number of metal ions which are coordinately bound to the substrate is measured by an ICP analysis apparatus or the like. The number of chelators per unit area can be determined from the number of metal ions and the area of the base material onto which the chelators are bound. In the case that calculation of the chelator density is performed, the number of chelators per unit area can be determined by utilizing a calculating software program such as CHEM 3D (by Cambridge Soft) to obtain the volume of the chelators. In the case that the area occupied by the chelators is obtained by a calculating software program and the chelator is NTA, for example, an estimated volume of approximately $0.25\ nm^2$ is obtained. Therefore, it is theoretically difficult to cause the chelators to be bound to the base material at a density higher than $4/nm^2$. Note that the chelator density may also be determined by measuring the number of immobilized metal ions.

It is preferable for a base to be employed as an additive during binding of the chelators. The binding rate of the chelators can be improved by employing the base. Examples of the base include: DBU (1,8-diazabicyclo[5,4,0]undec-7-ene); DBN (1,5-diazabicyclo[4,3,0]non-5-ene); imidazole, methyl imidazole; pyrimidine; pyridine; N,N-dimethyl-4-amino pyridine; picoline; 2,6-lutidine quinoline; triethyl amine; diisopropyl ethyl amine; dimethyl phenylamine; DABCO (1,4-diazabicyclo[2,2,2]octane); sodium hydroxide; potassium hydroxide; and cesium hydroxide. The base to be employed may be selected as appropriate according to the organic solvent to be employed.

It is preferable for the amount of the base to be within a range from 1 mol % to 10,000 mold with respect to the amount of chelators to be bound, more preferably within a range from 100 mol % to 1,000 mol %, and most preferably within a range from 300 mol % to 500 mol %.

(4) Metal Ions

Any metal ion may be employed as the metal ions, as long as they form unsaturated metallic complexes. From the viewpoint of stability of obtained metallic complexes, transitional metal ions are preferred. Specifically, appropriate metal ions may be selected from among a group consisting of: Cu(I); Cu(II); Ni(II); Co(II); Co(III); Fe(II); Fe(III); and Ga(III), according to the type of chelator. Among these metal ions, Cu(II), Ni(II), Co(III), and Fe(III) are preferred, and Cu(II) is particularly preferred.

Regarding combinations of the metal ions and the chelator density, it is preferable for the chelator density to be $0.8/nm^2$ or greater in the case that the metal ions are Cu(II) ions.

(5) Bioactive Substance

Examples of the bioactive substance include: immunoproteins; enzymes; microorganisms; nucleic acids; low molecular weight organic compounds; anti-immunoproteins; immunoglobulin binding proteins; glycobinding proteins; sugar chains that recognize sugars; fatty acids; fatty acid esters; polypeptides having ligand binding potential; and oligopeptides having ligand binding potential. These bioactive substances are immobilized on the substrate by coordinate bonding with the metal ions, and have functional groups which are capable of being coordinated with respect to the metal ions. That is, the bioactive substances have metallic coordinating properties. The metallic coordinating properties can be easily imparted, by covalent bonding with ligands having strong coordinating forces.

The functional group may be any functional group, as long as it has a nitrogenous heterocyclic ring, and is capable of forming metallic complexes with the metal ions. The nitrogenous heterocyclic ring may be a monocycle or a condensed three to seven member ring including at least one nitrogen atom. Preferably, the nitrogenous heterocyclic ring is a five member ring or a six member ring.

Examples of ligands having such nitrogenous heterocyclic rings include: pyrrole; imidazole; pyrazole; oxazole; isooxazole; triazole; isothiazole; 1,2,3-triazole; 1,2,4-triazole; 1,3,4-thiadiazole; tetrazole; pyridine; pyrazine; pyrimidine; pyridazine; 1,2,3-triazine; 1,2,4-triazine; 1,3,5-triazine; 1,2,4,5-tetrazine; azepine; azonine; quinoline; isoquinoline; acridine; phenanthridine; indole; isoindole; carbazole; benzimidazole; 1,8-naphthyridine; purine; pteridine; benzotriazole; quinoxaline; quinazoline; perimidine; cinnoline; phthaladine; 1,10-phenanthroline; phenoxazine; phenothiazine; phenazine; 8-hydroxyquinoline; 8-mercaptoquinoline; 2,2'-bipyridine; 2,2'-dipyridyl amine; di (2-picolyl amine); 2,2',2"-terpyridine; porphyrin; phthalocyanine; and derivatives thereof. Among the above ligands, pyrrole, imidazole, pyrazole, oxazole, thiazole, pyridine, and derivatives thereof are preferable, from the viewpoint of improving the stability of the obtained metallic complexes.

Particularly, imidazole groups are preferred as the functional group, due to the ease of introduction thereof using amino acid automatic synthesis systems or genetic modification. It is preferable for so called His-tags, in which histidines (His) including imidazole groups are introduced as functional sites, to be long. It is preferable for the number of imidazole groups to be within a range from 6 to 100, more preferably within a range from 10 to 20, and most preferably within a range from 10 to 14. If the number of imidazole groups is small, it becomes difficult to hold bioactive substances at multiple points, and if the number of imidazole groups is large, the size becomes great, and the activation of proteins may be adversely influenced. The histidines may be consecutive, such as His-His-His-His, and may also have different structures therebetween, such as His-His-(different structure)-His-His.

(6) Immobilization of the Bioactive Substance

The bioactive substance is immobilized, by coating the biosensor chip with a solution that includes the bioactive substance, then drying biosensor chip. In the present invention, "coating" includes immersion. In the case that the bioactive substance includes the nitrogenous heterocyclic rings, the nitrogenous heterocyclic rings form coordinate bonds with the metal ions and form chains, thereby immobilizing the bioactive substance.

When the metal ions and the nitrogenous heterocyclic rings of the bioactive substance are added to the chelators which are bound to the base material, (1) the chelators, (2) the nitrogenous heterocyclic rings of the bioactive substance, and (3) water molecules or hydroxide ions are coordinated on the metal ions to form chains.

For example, in the case that NIA is utilized as the ligands, and metal ions capable of six coordinates are added, (1) three carboxyl groups and one nitrogen atom of the NTA occupy four of the six coordinate sites, (2) a nitrogenous heterocyclic ring group of the bioactive substance occupies one of the two remaining coordinate sites, and (3) a water molecule or a hydroxide ion occupies the last remaining coordinate site, to form six coordinate complexes.

In the case that iminodiacetic acid is utilized as the ligands, and metal ions capable of six coordinates are added, (1) two carboxyl groups and one nitrogen atom of the iminodiacetic acid occupy three of the six coordinate sites, and (2) nitrogenous heterocyclic ring groups of the bioactive substance and (3) water molecules or hydroxide ions occupy the remaining three coordinate sites, to form six coordinate complexes.

Here, metal ions capable of six coordinates have been described as examples. However, the number of coordinate sites may be seven or greater, or five or less. In addition, the carboxyl groups that form the complexes need not be provided by a single ligand, but from a plurality of ligands.

(7) Production of the Substrate

Hereinafter, the steps for producing the substrate according to the embodiment of the present invention will be described with reference to the attached drawings. FIG. 2 is a collection of schematic diagrams that illustrate the steps from formation of the metal film to binding of the chelators onto the self assembling monolayer. FIG. 3 is a collection of schematic diagrams that illustrate the steps from immobilization of the metal ions onto the chelators to immobilization of the bioactive substance thereon. Note that The chelators are magnified in FIG. 3 to clearly illustrate bonding state of the metal ions and the immobilized state of the bioactive substances. NTA is employed as the ligands, Cu(II) is employed as the metal ions, and proteins having imidazole groups as function groups are employed as the bioactive substance (denoted by P in FIG. 3).

First, the metal film is formed on the base material (FIG. 2A). The metal film may be formed by known methods, such as: sputtering; vapor deposition; ion plating; electrolytic plating; and non-electrolytic plating. Note that as described previously, the intermediate layer of chrome or the like may be interposed between the base material and the metal film. Next, the SAM is formed on the metal film (FIG. 2B). As described previously, the SAM may be formed by immersing the base material, on which the metal film is formed, in a solution containing the aforementioned alkanethiol derivatives or the like.

Thereafter, the chelators are caused to bind with the SAM. In the case that the self assembling monolayer has carboxyl groups at the ends thereof, the chelators can be caused to bond with the carboxyl groups, by: activating the carboxyl groups; then causing the chelators to react therewith (FIG. 2C).

Figure 3A:
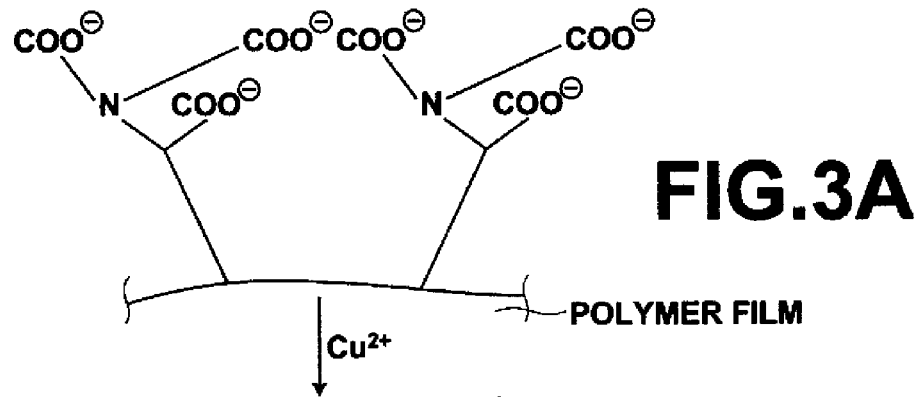
FIG. 3 is a schematic diagram that illustrates the steps for producing the substrate according to the embodiment of the present invention.
Figure 3B:
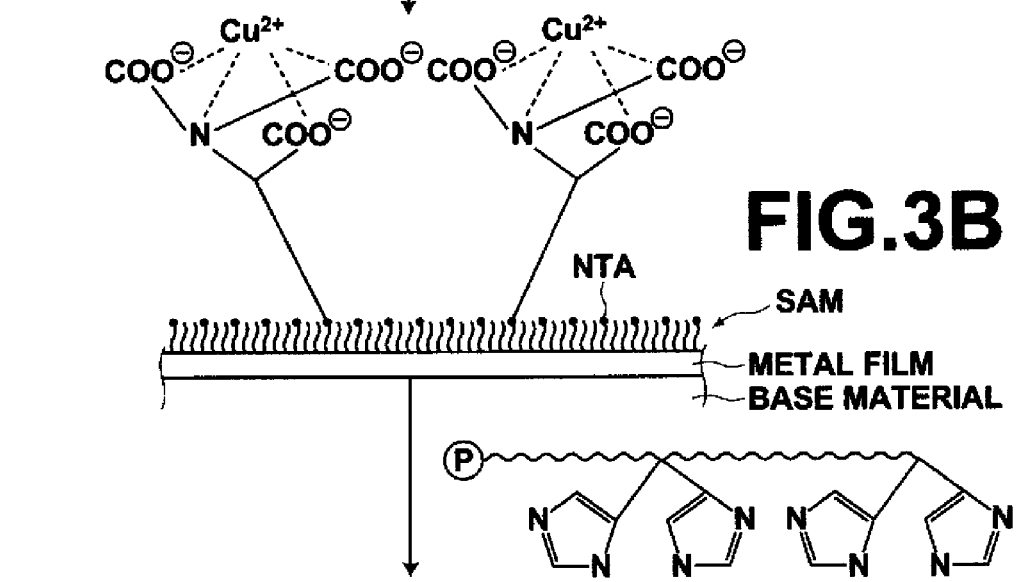
Figure 3C:
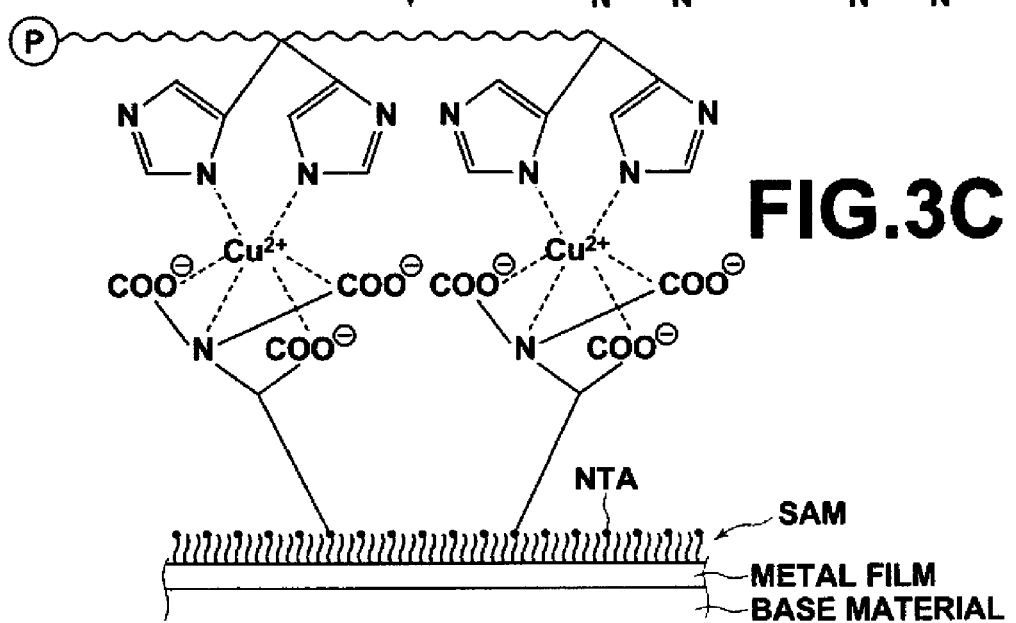

Using the NTA illustrated in FIG. 2C as an example of the chelators, single carboxyl groups of the SAM are substituted with three carboxyl groups (FIG. 3A). The Cu(II) ions are added, to form chains with the carboxyl groups of the NTA (FIG. 3B). Here, the coordination positions of the Cu(II) ions are not completely fulfilled by the NTA. If the protein having imidazole groups at the ends thereof is added to the NTA-Cu (II), the imidazole group coordinately bonds with the Cu(II) ions (FIG. 3C). Note that only four imidazole groups of the protein are illustrated in FIG. 3C, in order to facilitate viewing of the bound state. However, it is preferable for the number of imidazole groups to be within a range from 6 to 100, as described previously.

It is preferable for cleansing to be performed by a buffer or an imidazole solution, after immobilizing the protein having the imidazole groups at the ends thereof to the Cu(II) ions. The bioactive substance having the imidazole groups at the ends thereof can be purified, by removing protein which has not bound to the Cu(II) ions of the substrate, as well as other impurities. Note that in the case that Cu(II) ions are utilized as the metal ions, the holding strength of Cu(II) ions with respect to bioactive substances having imidazole groups at the ends thereof is high. Therefore, the bioactive substances having imidazole groups at the ends thereof will not be washed away, even if a large amount of imidazole solution is caused to flow on the substrate, and purification can be performed to achieve high purity.

(8) Applications of the Substrate of the Present Invention

The substrate of the present invention may be applied to biosensors and bioreactors (refer to Bioreactor Technology, K.K. CMC, 1988, and Biochips and Biosensors, Kyoritsu Publishing, K.K., 2006, for example). The term biosensor is broadly interpreted, and refers to sensors that convert interactions between biological molecules into signals such as electrical signals, to measure and/or detect target substances. Bioreactors are reactors that utilize biochemical reactions by biological catalysts, such as enzymes, germs, cells, and organelles, and are applied to produce useful substances, to produce energy, and to break down environmental pollutants. Hereinafter, each of the applications will be described.

(8-1) Application to Biosensors

Generally, biosensors are constituted by receptor sites that recognize chemical substances as detection targets, and transducer sites that convert physical or chemical changes at the receptor sites into electric signals. Substances within organisms that have affinities toward each other include: enzymes and ground substances; enzymes and coenzymes, antigens and antibodies; and hormones and receptors. Biosensors utilize the principle of selectively measuring one of a pair of substances which has an affinity toward the other substance by immobilizing the other substance onto a substrate, and employing the immobilized substance as a molecular discriminating substance.

For example, a surface plasmon resonance biosensor comprises a member having a portion that transmits and reflects light irradiated from a sensor, and a portion at which bioactive substances are immobilized. The substrate of the present invention may be employed as the portion at which the bioactive substances are immobilized.

The surface plasmon resonance phenomenon occurs due to the fact that the intensity of a monochromatic light beam, which is reflected at an interface between an optically transmissive material, such as glass, and a thin metal film layer, depends on the refractive index of a sample present at the light output side of the thin metal film layer. Accordingly, the sample can be analyzed by measuring the intensity of the reflected monochromatic light beam.

As a surface plasmon measuring apparatus that utilizes the fact that surface plasmon are excited by light waves to analyze substances, there is that employing a system called the "Kretschmann configuration" (see Japanese Unexamined Patent Publication No. 6 (1994)-167443, for example). The surface plasmon resonance sensor employing the "Kretschmann configuration" is equipped basically with a dielectric block formed, for example, into the shape of a prism; a metal film, formed on a surface of the dielectric block, for placing a sample thereon; a light source for emitting a light beam; an optical system for making the light beam enter the dielectric block at various angles of incidence so that the condition for total internal reflection is satisfied at the interface between the dielectric block and the metal film; and photodetecting means for detecting the state of the surface plasmon resonance, that is, the state of attenuated total reflection, by measuring the intensity of the light beam totally internally reflected at the interface.

In addition, a leaky mode sensor is known as a similar measuring apparatus that utilizes ATR, as disclosed, for instance, in "Spectral Researches," Vol. 47, No. 1 (1998), pp. 21-23 and pp. 26-27. The leaky mode sensor is constructed basically by: a dielectric block in the form of a prism, for example; a cladding layer formed on a surface of the dielectric block; an optical waveguide layer, formed on the cladding layer, for placing a sample thereon; a light source for emitting a light beam; an optical system for making the light beam enter the dielectric block at various angles of incidence so that the condition for total internal reflection is satisfied at the interface between the dielectric block and the cladding layer; and photodetecting means for detecting the excited state of the waveguide mode, that is, the state of ATR, by measuring the intensity of the light beam totally internally reflected at the interface between the dielectric block and the cladding layer. The substrate of the present invention may also be employed in leaky mode measuring apparatuses.

Further, the substrate of the present invention may be employed in a chip for a biosensor having a waveguide structure constituted by a diffraction grating and additional layers as necessary on a substrate. This type of biosensor detects changes in refractive index by using the waveguide structure. Details of biosensors of this type are described at page 4, line 48 through page 14, line 15, and FIGS. 1 through 8 of Japanese Patent Publication No. 6 (1994)-027703, and column 6, line 31 through column 7, line 47, and FIGS. 9A and 9B of U.S. Pat. No. 6,829,073. The biosensor chip of the present invention may also be employed in a modified version of this type of biosensor, in which arrays of diffraction grating waveguides are incorporated within wells of a microplate, such as that disclosed in PCT Japanese Publication No. 2007-501432. In the case that the diffraction grating waveguides are arranged in arrays at the bottom surfaces of the wells of a microplate, screening of drugs and chemical substances is enabled with high throughput.

(8-2) Application to Bioreactors

The substrate of the present invention can be applied as an insoluble substrate, on which enzymes are immobilized, of a bioreactor for producing useful compounds and for performing reactions (refer to Japanese Examined Utility Model Application Nos. 4 (1992)-018398, 4 (1992)-018399, and the like).

Embodiments of the substrate of the present invention will be described hereinafter.

Embodiment 1

(Production of the SAM)

A UV ozone treatment was administered to an Au sensor chip by Biacore, on which only a metal film is provided, for twelve minutes. Then, a 10 ml solution containing 50 μmol of 16-mercaptohexadecanoic acid by Aldrich in ethanol was prepared. The metal film was caused to react with the solution for twenty hours at 40° C. to form carboxyl groups on the metal film, then washed once with ethanol and once with ultrapure water.

(Binding of NTA)

50 μl of a solution, which was obtained by adding 1 mmol of EDC and 0.2 mmol of NHS to 1 ml of DMSO, was poured on the sensor chip, and caused to react therewith for 30 minutes at room temperature. The solution was removed, and the sensor chip was washed once with DMSO. Thereafter, the sensor chip was caused to react for two hours with a liquid, which was obtained by adding 0.1 mmol of AB-NTA by Dojin Chemical to 1 ml of DMSO. The solution was removed, and the sensor chip was washed once with ultra pure water, to produce a surface plasmon measuring chip.
(Immobilization of Protein)

The surface plasmon measuring chip produced as described above was set in Biacore 3000 by Biacore, which is a surface plasmon resonance apparatus. The biosensor chip was stabilized by an SPR HEPES buffer liquid (20 mM HEPES-HCl, 150 mM NaCl, pH 7.2) at a flow rate of 10 µl/min. 10 µl of a 1 mmol/L $CuSO_4$ aqueous solution was added. Thereafter, the surface plasmon measuring chip was washed with an HBS-N buffer for ten minutes. Then, 10 µl of a 1 µmol/L His10-Ubiquitin by R&D Systems (ubiquitin, in which series of ten histidine units are linked) was added, and the residual rate of protein was measured from the refractive index one minute after adding the solution and the refractive index one hour after adding the solution.
(Measurement of Non Specific Adsorption)

The surface plasmon measuring chip was set in Biacore 3000 by Biacore, which is a surface plasmon resonance apparatus. The biosensor chip was stabilized by an SPR HEPES buffer liquid (20 mM HEPES-HCl, 150 mM NaCl, pH 7.2) at a flow rate of 10 µl/min. Then, 30 µl of a 2 µmol/L His6-Ubiquitin by Novus Biologicals (ubiquitin, in which series of six histidine units are linked). Thereafter, the surface plasmon measuring chip was washed with 10 µl of a 10 mM NaOH aqueous solution, and the amount of His6-ubiquitin which was non specifically adsorbed was measured.

Embodiment 2

A surface plasmon measuring chip was produced in the same manner as that for Embodiment 1, except that 0.1 mmol of AB-NTA, by Dojin Chemical, 0.06 ml of DBU by Tokyo Kasei, and 0.94 ml of DMSO were employed in the step (Binding of NTA) instead of the solution obtained by adding 0.1 mmol of AB-NTA to 1 ml of DMSO. The residual rate of protein and the amount of non specific adsorption were measured in the same manner as that for Embodiment 1.

Embodiment 3

A surface plasmon measuring chip was produced in the same manner as that for Embodiment 1, except that a 10 mmol/L $NiCl_2$ aqueous solution was used in the step (Immobilization of Protein) instead of the 1 mmol/L $CuSO_4$ aqueous solution. The residual rate of protein and the amount of non specific adsorption were measured in the same manner as that for Embodiment 1.

Comparative Example 1

A UV ozone treatment was administered to an Au sensor chip by Biacore, on which only a metal film is provided, for twelve minutes. Then, a 10 ml solution containing 50 µmol of Dithiobis by Dojin Chemical (a SAM reagent having NTA at the ends thereof) was prepared. The metal film was caused to react with the solution for twenty hours at 40° C., then washed once with ethanol and once with ultrapure water, to produce a substrate having NTA bound to the metal film thereof. The steps (Immobilization of Protein) and (Measurement of Non Specific Adsorption) were performed in the same manner as those of Embodiment 1, and the residual rate of protein and the amount of non specific adsorption were measured in the same manner as that for Embodiment 1.

Comparative Example 2

A surface plasmon measuring chip was produced in the same manner as that for Embodiment 1, except that the 0.1 mmol of AB-NTA was dissolved in 1 ml of an NaOH aqueous solution in the step (Binding of NTA) instead of 1 ml of DMSO. The residual rate of protein and the amount of non specific adsorption were measured in the same manner as that for Embodiment 1.
(Chelator Density)

A 0.1M $NiCl_2$ aqueous solution was added to the surface plasmon measuring chips of Embodiments 1 through 3 and Comparative Examples 1 and 2 after NTA was bound thereon. The solution was removed after ten minutes, and the surface plasmon measuring chips were washed twice with ultra pure water. Two extracting operations were performed with 5 ml of a 50 mM EDTA aqueous solution. The extracted liquids were combined and the numbers of Ni ions were detected by measurement with an ICP analysis apparatus. The chelator density was determined based on the numbers of Ni ions and the area of the coated surface (50 $mm^2$).
(Density of Non Specific Adsorption Preventing Layer)

The refractive indices of unmodified metal films were measured by Biacore 3000 for the surface plasmon measuring chips of Embodiments 1 through 3 and Comparative Examples 1 and 2. The refractive indices of the metal films were measured again after the SAM's (non specific adsorption preventing layers) were formed thereon. The densities of the non specific adsorption preventing layers were calculated based on the differences in refractive indices (the same at the time that the NTA bound substrate is produced in Comparative Example 1) and the molecular weights of the non specific adsorbing molecules (16-mercaptohexadecanoic acid in Embodiments 1 through 3 and Comparative Example 2, and Dithiobis in Comparative Example 1).

The results are illustrated in Table 1. The amounts of non specific adsorption indicated in Table 1 are relative values when the amount of non specific adsorption for Comparative Example 2 is designated as 1. Note that the residual rates of proteins indicated in Table 1 were calculated, based on the refractive index measured by SPR one minute after adding the solutions and the refractive index measured by SPR one hour after causing the buffer to flow over the surface plasmon measuring chips, according to the formula (amount of immobilized protein one mite after adding solution/amount of immobilized protein one hour later).

TABLE 1

|  | Protein Residual Rate | Amount of Non Specific Adsorption | Density of Non Specific Adsorption Preventing Layer (per $nm^2$) | Chelator Density (per $nm^2$) |
| --- | --- | --- | --- | --- |
| Embodiment 1 | 3.6 | 0.7 | 4.0 | 0.4 |
| Embodiment 2 | 3.9 | 0.2 | 4.0 | 1.6 |
| Embodiment 3 | 3.8 | 0.2 | 4.0 | 1.6 |
| Comparative Example 1 | 2.6 | 2.0 | 1.6 | 1.6 |
| Comparative Example 2 | 1 | 1 | 4.0 | Less than 0.1 |

As is clear from Table 1, Embodiments 1 through 3, which have high chelators densities, have great protein holding functions and small amounts of non specific adsorption. In contrast, Comparative Example 1, which employed the SAM reagent having NTA at the ends thereof has a non specific adsorption preventing layer with a lower density, due to the bulkiness of the NTA causing gaps and defects to be formed in the SAM on the metal film. The amount of non specific adsorption was particularly high for Comparative Example 1. Meanwhile, Comparative Example 2, which has a non specific adsorption preventing layer with the same density as those of the Embodiments and a lower chelator density, the residual rate of protein, that is, the holding function with respect to protein after an hour, was low.

As described above, the chelators are bound to the self assembling monolayer at a density within a range from $0.4/nm^2$ to $4/nm^2$ in the substrate of the present invention. Therefore, it is possible for the chelators to hold bioactive substances at multiple points, and the bioactive substances can be stably immobilized. In addition, the substrate of the present invention has the self assembling monolayer formed by the self assembling molecules. Therefore, the self assembling monolayer is packed onto a metal film in an organized state, without any gaps or defects in the SAM on the surface of the metal film, and it is possible to suppress non specific adsorption.

The present invention may be utilized as a substrate onto which bioactive substances are immobilized. More specifically, the present invention may be utilized as a substrate for biosensor chips and bioreactor chips.

What is claimed is:

1. A method for producing a substrate, the substrate comprising a base material, a self assembling monolayer formed by self assembling molecules bound onto a surface of the base material, and chelators bound onto the self assembling monolayer, the method comprising the steps of:
    bonding the self assembling monolayer formed by the self assembling molecules onto the surface of the base material; and
    bonding the chelators onto the self assembling monolayer, the bonding of the chelators onto the self assembling monolayer being performed within an organic solvent and in the presence of a base,
    the chelators being bound to the self assembling monolayer at a density within a range of from $0.4/nm^2$ to $4/nm^2$ and the substrate comprising a non specific adsorption preventing layer having a density greater than $1.6/nm^2$, wherein the self assembling molecules have at one end a functional group selected from the group consisting of —SH (thiol), —SS (sulfide), —SeH (selenol), —SeSe (diselenide), and —COSH (thioic acid).

2. The method for producing a substrate as defined in claim 1, wherein the organic solvent is an aprotic polar solvent and the base comprises 1,8-diazabicyclo[5,4,0]undec-7-ene (DBU).

3. The method for producing a substrate as defined in claim 2, wherein the aprotic polar solvent is selected from the group consisting of dimethyl sulfoxide and N,N-dimethylformamide.

4. The method for producing a substrate as defined in claim 1, wherein the chelators are nitrilotriacetic acid derivatives.

5. The method for producing a substrate as defined in claim 1, wherein the chelators are bound to the self assembling monolayer at a density within a range of from $1/nm^2$ to $4/nm^2$.

6. The method for producing a substrate as defined in claim 1, wherein metal ions are immobilized onto the chelators.

7. The method for producing a substrate as defined in claim 6, wherein bioactive substances are immobilized onto the metal ions.

8. The method for producing a substrate as defined in claim 7, wherein the metal ions are transition metal ions.

9. The method for producing a substrate as defined in claim 8, wherein the transition metal ions are Cu(II) ions.

10. The method for producing a substrate as defined in claim 8, wherein the bioactive substances have functional groups that coordinately bond with the transition metal ions, and are immobilized onto the transition metal ions by the functional groups.

11. The method for producing a substrate as defined in claim 9, wherein the bioactive substances have functional groups that coordinately bond with the Cu(II) ions, and are immobilized onto the Cu(II) ions by the functional groups.

12. The method for producing a substrate as defined in claim 10, wherein the functional groups are imidazole groups.

13. The method for producing a substrate as defined in claim 11, wherein the functional groups are imidazole groups.

* * * * *